United States Patent [19]
Wrobel et al.

[11] Patent Number: 5,574,051
[45] Date of Patent: Nov. 12, 1996

[54] CERTAIN-[3-ARYL-PROP-2-YNYL]-5-(ARYLSULFONYL) THIAZOLIDINE-2,4-DIONE DERIVATIVES

[75] Inventors: Jay E. Wrobel, Lawrenceville; Zenan Li, Plainsboro; Arlene J. Dietrich, Delran, all of N.J.

[73] Assignee: American Home Products Corporation, Madison, N.J.

[21] Appl. No.: 449,063

[22] Filed: May 24, 1995

Related U.S. Application Data

[62] Division of Ser. No. 207,980, Mar. 8, 1994, abandoned.

[51] Int. Cl.$^6$ ............... A61K 31/44; C07D 417/06; C07D 417/12
[52] U.S. Cl. ........................... 514/340; 546/269.7
[58] Field of Search .................. 546/280, 269.7; 514/340

[56] References Cited

U.S. PATENT DOCUMENTS

| | | | |
|---|---|---|---|
| 4,461,902 | 7/1984 | Kawamatsu et al. | 548/183 |
| 4,687,777 | 8/1987 | Meguro et al. | 514/342 |
| 4,738,972 | 4/1988 | Eggler et al. | 514/314 |
| 4,743,611 | 5/1988 | Malamas et al. | 514/390 |
| 4,997,948 | 3/1991 | Zask et al. | 548/183 |
| 5,068,342 | 11/1991 | Zask et al. | 548/183 |

FOREIGN PATENT DOCUMENTS 0084926  8/1983  European Pat. Off. .

OTHER PUBLICATIONS

Hulin, et al., J. Med. Chem., 35, 1853–1864 (1992).
Sohda et al., J. Med. Chem., 35, 2617–2626 (1992).
Zask, et al., J. Med. Chem., vol. 33, No. 5, 1418–1423 (1990).
Chem Abstract, 89: 179986p, "3–Substituted–1,3–thiazolidine–2,4–diones" Nov. 1978.
Chem Abstract, 74: 61927g, "Effect of 3–phenylthiazolidine–2,4–dione Derivatives on Some Myobacteria" Mar. 1971.
Yoshioka et al., J. Med. Chem., 32, 421–428 (1989).
Sohda et al., Arzneim–Forsch./Drug Res., 40, 37–42 (1990).
Stevenson, et al., Metabolism, vol. 40, No. 12 (Dec. 1991), 1268–1274.
Mohrbacher et al., Annual Reports in Medicinal Chemistry, vol. 22, 1987, pp. 213–222.
Fujita et al., Diabetes, vol. 32 (Sep. 1983), 804–810.
Chem Abstract, 89: 197526t, "Antifouling 3–amino–1, 3–thiazolidine–2,4–diones" Dec. 1978.

*Primary Examiner*—Alan L. Rotman
*Attorney, Agent, or Firm*—Steven R. Eck

[57] ABSTRACT

This invention relates to novel 5-[3-aryl-prop-2-ynyl]-5-(arylsulfonyl)- thiazolidine-2,4-diones and 5-[3-aryl-prop-2-ynyl]-5-(arylsulfanyl)thiazolidine-2,4-diones characterized by the general formula (I), seen below, wherein Ar is phenyl, 2-naphthyl, alkyl substituted phenyl, alkoxy substituted phenyl, halogen substituted phenyl, 2-phenyl, substituted 2-pyridinyl, 3-pyridinyl, 4-pyridinyl, 2-quinolinyl, 2-pyrimidinyl, 2-benzoxazolyl, 2-benzthiazolyl, 2-benzimidazolyl, 2-furanyl, 2-benzo-[b]-furanyl, 2-thienyl, 2-benzo-[b]-thienyl; n is 0 or 2; and Ar' is phenyl, alkyl substituted phenyl, perfluoroalkyl substituted phenyl, halogen substituted phenyl, alkoxy substituted phenyl, perfluoroalkoxy substituted phenyl and alkylio substituted phenyl.

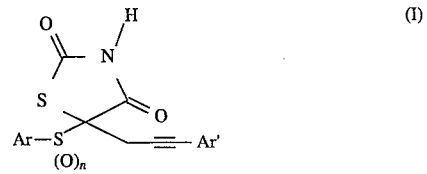

(I)

This invention also relates to the use of the abovementioned compounds in lowering the blood glucose levels in hyperglycemic mammals and pharmaceutical compositions containing the same.

9 Claims, No Drawings

CERTAIN-[3-ARYL-PROP-2-YNYL]-5-(ARYLSULFONYL) THIAZOLIDINE-2,4-DIONE DERIVATIVES

This is a division of application Ser. No. 08/207,980 filed Mar. 8, 1994, abandoned.

The present invention provides novel compounds possessing antihyperglycemic activity. More particularly, the present invention provides novel 5-[3-aryl-prop-2ynyl]-5-(arylsulfonyl)-thiazolidine-2,4-diones and 5-[3-aryl-prop-2-ynyl]-5-(aryl-sulfanyl)thiazolidine-2,4-diones, and derivatives thereof, which are useful in lowering the blood glucose level in hyperglycemic mammals and useful in the treatment of noninsulin dependent (type 2) diabetes mellitus, preferably in humans.

BACKGROUND

Treatment for non-insulin dependent diabetes mellitus (Type 2 diabetes) usually consists of a regimen of diet and exercise, oral hypoglycemic agents and, in more severe cases, insulin. Oral agents common use are the sulfonylureas and biguanides. While the sulfonylureas are valuable for the treatment of Type 2 diabetes, they may give rise to hypoglycemic episodes and exhibit other toxic manifestations which limit their use. They are also prone to a high incidence of primary and secondary failures of efficacy. Similarly, the use of biguanides has declined because of their association with incidents of toxic lactic acidosis. A continuing need for new hypoglycemic agents which may be less toxic and more efficacious is clearly evident.

5-[(1-and 2-naphthalenyl)sulfonyl]-2,4-thiazolidinediones (Zask and Jirkovsky U.S. Pat. No. 4,997,948, 1991), 5-[(1-and 2-naphthalenyl)thio]-2,4-thiazolidinediones (Zask and Jirkovsky U.S. Pat. No. 5,068,342, 1991) and 5-[arylsulfonyl]-2,4-thiazolidinediones (Zask et al, J. Med. Chem. 1990, 33, 1418–1423) were previously disclosed as antidiabetic agents. The compounds of the present invention, (I), differ in that they also contain a 5-[3-aryl-prop-2-ynyl] group. This latter moiety enhances the antidiabetic potency of 5-arylsulfonyl-2,4-thiazolidinediones. 2-[(4-Methylphenyl)-sulfonyl]-5-phenylpent-4-ynoic acid (BM13907), (A) (Wolff, et al. U.S. Pat. No. 4,933,367, 1990; Freund, et al. Arch. Pharmacol. 1989, 340 (suppl R40) Abstract 117; Obermaier-Kusser Biochem. J. 1989,261,699).was also disclosed as antidiabetic agent. The compounds of the present invention, (I), differ in that they contain a 2,4-thiazolidinedione ring in place of a carboxyl group of A.

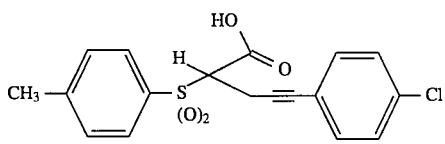

Other disclosures claim compounds which contain a 2,4-thiazolidinedione ring and also show antidiabetic activity. These include ciglitazone (U.S. Pat. No. 4,461,902; Sohda, et al. Chem. Pharm. Bull. 1982, 30, 3580) and a number of more potent analogs: pioglitazone (Sohda, et al. Arzneim.-Forsch./Drug. Res. 1990, 40, englitazone (Stevenson, et al. Metabolism 1991, 40, 1268); CS-045 (Metabolism 991, 40, 1213) and others (Hulin, et. al. J. Med. Chem. 1992, 35, 1853; Sohda, et al. J. Med. Chem. 1992, 35, 2617). None of the 2,4-thiazolidinedione containing compounds from the above disclosures contain the 5-(arylsulfonyl), 5-(arylsulfanyl) or 5-[3-aryl-prop-2-ynyl] groups possessed by the compounds of the present invention.

Compounds in which sulfur is attached to the 5-position of a 2,4-thiazolidinedione ring have been disclosed (Japan Kokai 78 40, 770; Japan Kokai 78 46, 973; Mikrobiol. Zh. (Kiev) 1970, 32, 518–520 (Ukrain); Ger. Often. DE 3,045, 059) but differ from the compounds of the present invention in that the nitrogen of the 2,4-thiazolidinedione ring is substituted or the sulfur is in the form of a sulfonic acid. In addition, these compounds are not sulfones and do not contain a napthalene ring. Furthermore, these compounds are claimed as having only antifouling or antibiotic properties.

DESCRIPTION OF THE INVENTION

This invention relates to novel 5-[3-aryl-prop-2-ynyl]-5-(arylsulfonyl)-thiazolidine-2,4-diones and 5-[3-aryl-prop-2-ynyl]-5-(arylsulfanyl)thiazolidine-2,4-diones of formula (I). These compounds possess antihyperglycemic activity, which has been demonstrated in their ability to lower plasma glucose levels in the db/db (C57BL/KsJ) mouse and to lower plasma glucose levels and insulin levels in the ob/ob (C57B1/6J) mouse. Both are models of human non-insulin dependent (type 2) diabetes mellitus.

The compounds of this invention are characterized by the general formula (I), seen below, wherein Ar is phenyl, 2-naphthyl, alkyl substituted phenyl, alkoxy substituted phenyl, halogen substituted phenyl, 2-pyridinyl, substituted 2-pyridinyl, 3-pyridinyl, 4-pyridinyl, 2-quinolinyl, 2-pyrimidinyl, 2-benzoxazolyl, 2-benzthiazolyl, 2-benzimidazolyl, 2-furanyl, 2-benzo-[b]-furanyl, 2-thienyl, 2-benzo-[b]-thienyl; n is 0 or 2; and Ar' is phenyl, alkyl substituted phenyl, perfluoroalkyl substituted phenyl, halogen substituted phenyl, alkoxy substituted phenyl, perfluoroalkoxy substituted phenyl and alkylthio substituted phenyl.

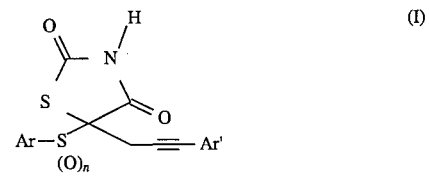

Preferred compounds of this invention include compounds of formula (I) in which Ar is phenyl, alkyl substituted phenyl, halogen substituted phenyl or 2-pyridinyl, n is 2; and Ar' is phenyl, halogen substituted phenyl and perfluoroalkoxy substituted phenyl.

The most preferred compounds of this invention include:

5-[3-(4-Chlorophenyl)-prop-2-ynyl]-5-(pyridine-2-sulfonyl)-thiazolidine-2,4-dione, 5-[3-(4-Fluorophenyl)-prop-2-ynyl]-5-(pyridine-2-sulfonyl)-thiazolidine-2,4-dione, 5-[3-(4-Chlorophenyl)-prop-2-ynyl]-5-(4-fluorobenzenesulfonyl)-thiazolidine2,4-dione, 5-(4-Fluorobenzenesulfonyl)-5-[3-(4-fluorophenyl)-prop-2-ynyl]-thiazolidine2,4-dione, 5-Benzenesulfonyl-5-[3-(4-chlorophenyl)-prop-2-ynyl]-thiazolidine-2,4-dione  5-Benzenesulfonyl-5-[3-(3,5-bis-trifluoromethyl-phenyl)-prop-2-ynyl]-thiazolidine-2,4-dione, 5-[3-(4-Chlorophenyl)-prop-2-ynyl]-5-(4-chlorobenzenesulfonyl)-thiazolidine-2,4-dione, 5-[3-(4-Bromophenyl)-prop-2-ynyl]-5-(toluene-4-sulfonyl)-thiazolidine-2,4dione, and 5-[3-Phenyl-prop-2-ynyl]-5-(toluene-4-sulfonyl)-thiazolidine-2,4-dione.

The compounds of this invention can be prepared according to the methods outlined in Schemes I through V, the first of which is presented below:

Scheme I

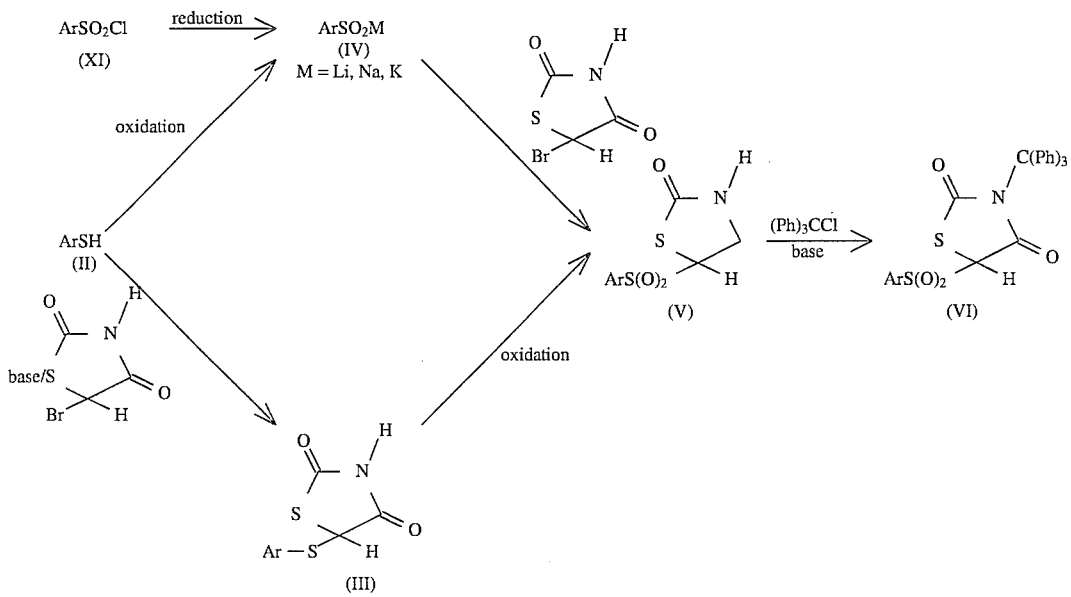

In Scheme I, the appropriate, commercially available arylthiol of formula (II) is reacted with a base and the subsequent complex is reacted with one or more equivalents of 5-bromo-thiazolidine-2,4-dione (Zask et at, *J. Med. Chem.* 1990, 33, 1418–1423) to produce a 5-arylsulfanyl-thiazolidine-2,4-dione of formula (III). The reaction is conveniently performed in an aprotic solvent such as THF or hexane using 2 or more equivalents of a strong metal amide base such as lithium diisopropyl amide or lithium bis(trimethylsilyl)amide at low temperatures (e.g. 0° to −78° C.) followed by warming to ambient or higher temperatures for 1 to 10 h. Alternatively the compound of formula (III) may be prepared in a protic solvent, such as water or a low molecular weight alcohol solvent. When done in this manner, the arylthiol of formula (II) is reacted with or more equivalents of an alkali metal carbonate or bicarbonate base such sodium carbonate or potassium bicarbonate at 0° C to room temperature. One or more equivalents of 5-bromo-thiazolidine-2,4-dione is added and reaction times vary from 1 h to 2 days.

The compound of formula (III) can then be oxidized to afford 5-arylsulfonyl-thiazolidine-2,4-dione of formula (V). Following the procedure of Zask et al (*J. Med. Chem.* 1990, 33, 1418–1423), this oxidation is conveniently performed using excess (2 to 20 equivalents) aqueous hydrogen peroxide in acetic acid at ambient or higher (30° to 80° C.) reaction temperatures for 1 to 10 h. Alternatively, potassium peroxymonosulfate will also accomplish the requisite oxidation effectively. Potassium peroxymonosulfate (KHSO$_5$) is sold commercially as a 2:1:1 complex with inert ingredients, potassium hydrogen sulfate (KHSO$_4$) and potassium sulfate (K$_2$SO$_4$). This complex is sold under the tradename oxone. The compound of formula (III) is dissolved in a low molecular alcohol solvent such as methanol and added to an aqueous solution of oxone that contains 2 or more equivalents of active ingredient KHSO$_5$. The reaction temperature can vary from 0° C. to 50° C. and the reaction time can vary from 30 min. to 2 days. Still alternatively, a perbenzoic acid reagent such as meta-chloroperbenzoic acid can be used to convert the compound of formula (III) to the compound of formula (V). Two or more equivalents of the perbenzoic acid are used, preferably in a halocarbon solvent such as chloroform at ambient temperatures for a period of from 1h to several days.

The compound of formula (V) may also be prepared by reacting one or more equivalents of an alkali metal arylsulfinate of formula (IV) with 5-bromo-thiazolidine-2,4-dione. Suitable solvents for this transformation include polar aprotic solvents such as DMF, THF and protic solvents such as low molecular weight alcohols or water. Alternatively the alkali metal arylsulfinate of formula (IV) can be reacted with 5-bromo-thiazolidine-2,4-dione using the phase transfer catalyst Aliquat 336 (tricaprylylmethylammonium chloride) according to the procedure of G. Baum, et al. (*Synthesis* 1987, 56–59).

The alkali metal sulfinate of formula (IV) can be conveniently prepared by oxidation of the arylthiol of formula (II) with 2 equivalents of aqueous hydrogen peroxide in the presence of an alkali metal hydroxide such as sodium hydroxide in water or in an aqueous low. molecular weight alcohol solvent. The alkali metal arylsulfinate of formula (IV) can also be prepared by reduction of an arylsulfonyl chloride of formula (XI). This transformation is most conveniently accomplished using the procedure of Chew Lee and Lamar Field (*Synthesis* 1990, 391–397) in which the sulfonyl chloride of formula (XI) is reacted with two equivalents of p-thiocresol and two equivalents of triethylamine in dichloromethane at −78° C. to room temperature. The arylsulfinic acid obtained upon aqueous acid workup is then treated with an alkali metal hydroxide to produce the alkali metal arylsulfinate of formula (IV).

The compounds of formula (V) have two primary sites which can be alkylated with alkylation agents in the presence of a base. These sites are the thiazolidinedione C-5 carbon atom and the thiazolidinedione nitrogen atom. The desired point of alkylation for compounds of the present invention is the C-5 carbon atom of (V). In order to prevent potential competition with alkylation at the nitrogen atom of (V), the nitrogen can be protected with a suitable alkylation protecting group. The trityl (triphenylmethane) group performs this function. The trityl group is introduced by reacting the compound of formula (V) with one molar equivalent of triphenylmethane chloride in the presence of one molar equivalent of a tertiary amine base, such as triethylamine, preferably in a halocarbon solvent at 0° C. or ambient temperatures.

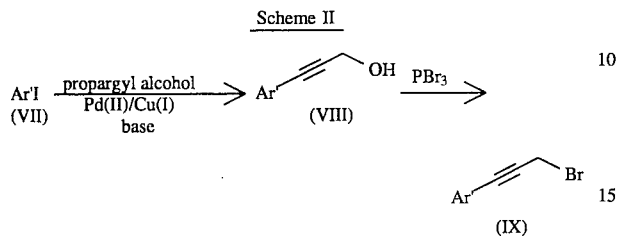

Scheme II

In Scheme II, the (3-arylprop-2-ynyl)-bromides Of formula (IX) can be prepared via a two step process from commercially available aryliodides of formula (VII). In the first step, the compound of formula (VIII) is prepared by the reaction of the compound of formula (VII) with one or more equivalents of propargyl alcohol, in the presence of a catalytic amount of a palladium (II) reagent such as dichlorobis(triphenylphosphine) palladium (II) and a catalytic amount of a copper (I) reagent such as copper (I) iodide. This reaction is also performed in the presence of one or more equivalents of a secondary or tertiary amine such as diethylamine or triethylamine. The secondary or tertiary amine may be used as solvent or a halocarbon solvent such as chloroform may be employed. Ambient temperature up to 80° C. are commonly used reaction temperatures with reaction times varying from 1 h to 2 days. The compound of formula (IX) is then most conveniently prepared from the compound of formula (VIII) by reacting (VIII) with 0.5 to one molar equivalent of phosphorus tribromide in dry ether solvent containing pyridine. This reaction is most conveniently done at 0° C. to room temperature for a period of from 1 h to 30 h.

The compounds of formula (I) are then prepared by alkylation of the compounds of formulas (III), (V) or (VI) with the compounds of formula (IX).

Referring to Scheme III:

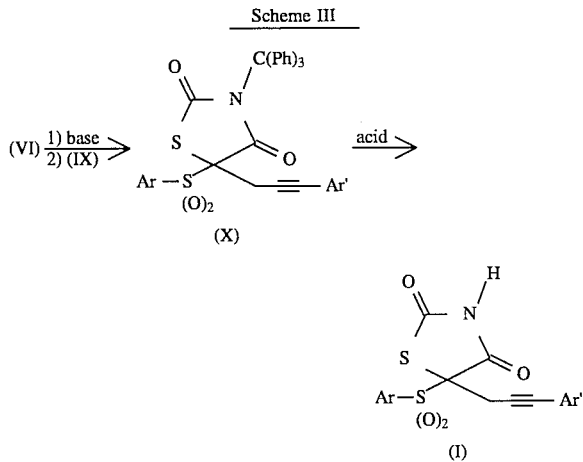

Scheme III the thiazolidinedione C-5 hydrogen of (VI) is removed by the action of one or more equivalents of a base. Commonly used bases include alkali metal hydrides such as sodium hydride alkali metal, alkali metal alkyls such as butyl lithium or alkali metal amides such as lithium diisopropylamide. Suitable solvents include THF or DMF with temperatures ranging from −78° C. to room temperature. After deprotonation of the compound of formula (VI), the bromide of formula (IX) is introduced and the reaction is typically stirred at 0° C. or room temperature for 1 to 48 h to produce the compound of formula (X). The compound of formula (X) is then treated with an acid to remove the triphenylmethane protecting group. Typical acids include one or more equivalents of trifluoroacetic acid or formic acid. This acid may be used as solvent or a halocarbon solvent such as dichloromethane is commonly employed. This reaction is conveniently done at 0° C. or room temperature for periods of from 10 min. to 2 h.

Referring to Scheme IV:

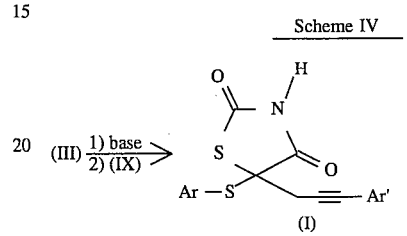

Scheme IV

5-[3-aryl-prop-2-ynyl]-5-(arylsulfanyl)-thiazolidine-2,4-diones of formula (I) may prepared by reaction of the appropriate 5-(arylsulfanyl)-thiazolidine-2,4-diones of formula (III) with 2 or more equivalents of a base. Two equivalents of base effect deprotonation of both the thiazolidinedione nitrogen atom and at the C-5 position to form a dianion. Common bases to accomplish this deprotonation include alkali metal hydrides such as sodium hydride, alkali metal alkyls such as butyl lithium or alkali metal amide bases such as lithium diisopropylamide or lithium bis(trimethylsilyl)amide. Convenient solvents include THF for alkali metal amide bases and THF or DMF for the alkali metal hydride bases. Reaction temperatures vary from −78° C. to room temperature. Two minutes to 1 h after the base is introduced, one or more equivalents of the appropriate (3-arylprop-2-ynyl)-bromide of formula (IX) is added to the reaction mixture and the reaction is allowed to stir at 0° C. or room temperature for a period of from 1 h to 3 days. Alkylation occurs exclusively on the thiazolidindione C-5 carbon atom to afford the 5-[3-aryl-prop-2-ynyl]-5-(arylsulfanyl)-thiazolidine-2,4-dione of formula (I).

Referring to Scheme V:

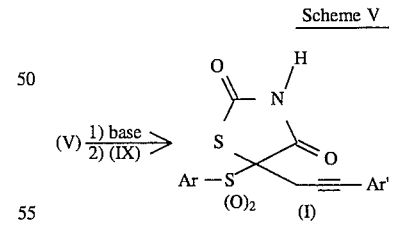

Scheme V

5-[3-aryl-prop-2-ynyl]-5-(arylsulfonyl)-thiazolidine-2,4-diones of formula (I) may be prepared by reaction of the appropriate 5-(arylsulfonyl)-thiazolidine-2,4-diones of formula (V) with 2 or more equivalents of a base. Two equivalents of base effect deprotonation of both the thiazolidinedione nitrogen atom and at the C-5 position to form a dianion. Common bases to accomplish this deprotonation include alkali metal hydrides such as sodium hydride, alkali metal alkyls such as butyl lithium or alkali metal amide bases such as lithium diisopropylamide or lithium bis(trimethylsilyl)amide. Convenient solvents include THF for alkali metal amide bases and THF or DMF for the alkali metal hydride bases. Reaction temperatures vary from −78° C. to room temperature. Two minutes to 1 h after the base is introduced, one or more equivalents of the appropriate (3-arylprop-2-ynyl)-bromide of formula (IX) is added to the reaction mixture and the reaction is allowed to stir at 0° C. or room temperature for lh to 3 days. Alkylation occurs exclusively on the thiazolidindione C-5 carbon atom to afford the 5-[3-aryl-prop-2-ynyl]-5-(arylsulfonyl)-thiazolidine-2,4-dione of formula (I).

The present invention also comprises a method for lowering the blood glucose level in a hyperglycemic mammal, comprising administering to such mammal an effective amount of one or more of the compounds disclosed herein effective to lower blood glucose. This method may also be seen as a method of treating hyperglycemia in a mammal which comprises administering to such mammal an effective amount of one or more of the compounds disclosed herein effective to lower blood glucose. The mammal so treated is preferably a human. The compounds of the present invention may also be used as agents for the treatment of hyperlipidemia and diabetic complications (e.g. neuropathy, nephropathy, ritinopathy, cataracts). Compounds of the present invention, in order to enhance efficacy, may also be used in combination with insulin, sulfonylureas, biguanides, aldose reductase inhibitors and hypolipidemic agents.

The dosages of the compounds presented herein will vary with the particular compound chosen and the form of administration. Furthermore, it will vary with the particular host under treatment. Generally, the compounds of this invention are administered at a concentration level that affords protective effects without any deleterious side effects. For example, the effective amount of compound can usually range from about 10 to about 250 mg/kg body weight per day administered once dally or divided into two to four administrations per week. The optimum dosage for the individual subject being treated will be determined by the person responsible for treatment, generally smaller doses being administered initially and thereafter increases in dosage are made to determine the most suitable dosage.

Also embraced by the present invention are pharmaceutical compositions useful for lowering blood glucose. Among these are compositions comprising a mixture of one or more of the compounds disclosed herein, or a pharmaceutically acceptable salt thereof, and a pharmaceutically acceptable carrier, which can be used according to the same methods of administration as the compounds, themselves.

The compounds of the present invention may form salts with suitable; therapeutically acceptable inorganic and organic bases. These derived salts possess the same activity as their parent acid and are included within the scope of this invention. Suitable inorganic bases to form these salts include, for example, the hydroxides, carbonates or bicarbonates of the therapeutically acceptable alkali metals or alkaline; earth metals such as lithium, sodium, potassium, magnesium, calcium and the like. Suitable organic bases include primary and secondary amines such as methylamine, benzathine (N,N¹-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) procaine, etc. Furthermore, there may be mentioned the quaternary salts, for example, the tetraalkyl (e.g. tetramethyl), alkyl-alkanol (e.g. methyltriethanol) and cyclic (e.g. N,N-dimethylmorpholine) ammonium salts. In principle, however, there can be used all the ammonium salts which are physiologically compatible.

Transformations to the corresponding salts are readily carded out by reacting: the acid form of the compounds with an appropriate base, usually one equivalent, in a cosolvent. The salt is isolated by concentration to dryness or by adding of a non-solvent. For example, in the case of inorganic salts, it is preferred to dissolve the acid or the compound in water containing a hydroxide, carbonate or bicarbonate corresponding to the inorganic salt desired. Evaporation of the solution or addition of a water-miscible solvent of more moderate polarity, for example, a lower alkanol such as butanol, or a lower alkanone such as ethyl methyl ketone, gives the solid inorganic salt. In the case of an amine salt, it is preferred to use a cosolvent of moderate or low polarity such as ethanol, ethylacetate and benzene. Evaporation of the solvent or addition of a miscible diluent of lower polarity such as benzene or n-hexane gives the; solid salt. Quaternary ammonium salts may be prepared by mixing the acid of the compound with a quaternary ammonium hydroxide in a water solution followed by evaporation of the water.

The compounds of the present invention may be clinically administered to mammals, including man, by either the oral or parenteral route. Oral administration may be either alone or in combination with a solid or liquid pharmaceutically acceptable carder or diluent such as starch, milk, sugar, certain types of clay, water, vegetable or mineral oils, and so forth to form tablets, capsules, powders, syrups, solutions, suspensions, and the like. For parenteral administration, the active compounds may be used in combination with aqueous or organic media to form injectable solutions or suspensions. For example, solutions in sesame or peanut oil, aqueous solutions of water and soluble pharmaceutically acceptable salts of the compounds. The injectable solutions prepared in this manner may be administered intravenously, intraperitoneally, subcutaneously or intramuscularly. The compounds of this invention may also be administered in the form of suppositories.

The following nonlimiting examples further illustrate this invention.

EXAMPLE 1

5-(Toluene-4-sulfanyl)-thiazolidine-2,4-dione, (III)

To a solution of 5-bromo-thiazolidine-2,4-dione (5.0 g, 25.5 mmol, Zask et al *J. Med. Chem.* 1990, 33, 1418–1423) and p-thiocresol [(II), 3.17 g, 25.5 mmol] in dry THF (200 mL) at −78° C. was added lithium bis(trimethylsilyl)amide (1.0M in hexanes, 56 mL, 56 mmol) dropwise. After 30 min. the reaction mixture was warmed to room temperature. After an additional hour, 2N HCl was added to pH=1. The layers were separated and the aqueous phase was extracted with ethyl acetate (3×300 mL). The combined organic phase was dried (MgSO$_4$), concentrated and flash chromatographed (3:2 petroleum ether: ethyl acetate) to provide the tire compound as a white solid (4.4 g, 72%): mp 124°–126° C.; NMR (CDCl$_3$): d8.08 (s, 1H, NH), 7.48 (d, J=8.7 Hz, 2H, Ar H), 7.18 (d, J=8.7 Hz, 2H, ArH), 5.32 (s, 1H, CH); MS(EI): 239 (MI, 90%), 196 (18%), 123 (100%).

EXAMPLE 2

5-(Pyridine-2-sulfanyl)-thiazolidine-2,4-dione, (III)

To a solution of 5-bromo-thiazolidine-2,4-dione (28.24 g, 0.144 mol) and 2-mercaptopyridine [(II), 16.0 g, 0.144 moll] in dry THF (200 mL) at −78° C. was added lithium bis(trimethylsilyl)amide (1.0M in hexanes, 317 mL, 0.317 mol) dropwise over a 40 min period. After 30 min. the reaction mixture was warmed to room temperature. After an additional 3 hr, 10% HCl was added to pH=1. The layers were separated and the aqueous phase was extracted with ethyl acetate (2×500 mL). The combined organic phase was washed with water (500 mL), brine (500 mL), dried (MgSO$_4$) and concentrated to provide the title compound as a green solid (30.45 g, 93%): mp 118°–120 ° C.; NMR (DMSO, d$^6$): δ 12.35 (s, 1H, NH), 8.39 (d, J=5.3 Hz, 1H, PyrH), 7.69 (dd, J=7.3, 8.3 Hz, 1H, PryH), 7.42 (d, J=8.3 Hz, 1H, PyrH), 7.19 (dd, J=5.3,7.3 Hz, 1H, PyrH), 6.31 (s, 1H, CH), MS(EI): 226 (MI, 12%), 155 (10%), 79 (100%); Anal. (C$_8$H$_6$N$_2$O$_2$S$_2$): C,H,N.

Using the procedure described in Example 1, the compounds of formula (III), Examples 3 and 4, were prepared from the appropriate arylmercaptan of formula (II) and 5-bromo-thiazolidine-2,4-dione.

EXAMPLE 3

5-(Quinoline-2-sulfanyl)-thiazolidine-2,4-dione, (III)

From 2-Quinolinethiol: mp 227°–229° C.

EXAMPLE 4

5-(Nanhthalene-2-sulfanyl)-thiazolidine-2,4-dione. (III)

(Known: Zask et al, *J. Med. Chem.* 1990,33, 1418–1423).

EXAMPLE 5

5-(4-Fluoronhenylsulfanyl)-thiazolidine-2,4-dione, (III)

5-Bromo-thiazolidine-2,4-dione (15.0 g, 76.5 mmol) was added to a 0° C., mechanically stirred solution of 4-fluorothiophenol [(II), 9.8 g, 76.5 mmol], sodium carbonate (27.75 g, 262 mmol) and water (120 mL). After 16 hr, the reaction mixture was diluted with water (500 mL), acidified with conc. HCl to pH=1 and filtered. The resultant solid was washed with water and petroleum ether and dried in vacuo to provide the title compound as a white solid (14.05 g, 75%): mp 99°–100° C.; NMR (DMSO, d$^6$): δ 12.14 (s, 1H, NH), 7.66 (t, J=8.0 Hz, 2H, ArH), 7.29 (t, J=8.5 Hz, 2H, Ar H), 6.05 (s, 1H, CH); MS(EI): 243 (MI, 100%), 200 (30%), 128 (60%), (50%); Anal. (C$_9$H$_6$FNO$_2$S$_2$): C,H,N.

Using the procedure described in Example 5, the compounds of formula (III), Examples 6–10, were prepared from the appropriate arylmercaptan of formula (II) and 5-bromo-thiazolidine-2,4-dione.

EXAMPLE 6

5-(Benzenesulfanyl)-thiazolidine-2,4-dione, (III)

From thiophenol: mp 103°–107.5° C.

EXAMPLE 7

5-(4-Chlorophenvlsulfanyl)-thiazolidine-2,4-dione, (III)

From 4-chlorothiophenol: mp 109°–110° C.

EXAMPLE 8

5-(4-Bromophenylsulfanyl)-thiazolidine-2,4dione, (III)

From 4-bromothiophenol: mp 115°–117° C.

EXAMPLE 9

5-(4-Methoxyphenylsulfanyl)-thiazolidine-2,4-dione, (III)

From 4-methoxythiophenol: mp 89°–91° C.

EXAMPLE 10

5-(Toluene-3-sulfanyl)-thiazolidine-2,4-dione, (III)

From m-thiocresol: mp 61.5°–64° C.

EXAMPLE 11

5-(4-Fluorophenylsulfonyl)-thiazolidine-2,4-dione, (V)

30 % Hydrogen peroxide (50.4 mL, 0.489 mol) was added dropwise over a 1 hr, 20 rain period to a mechanically stirred solution of 5-(4-fluorophenylsulfanyl)-thiazolidine-2,4-dione [(III), from Example 5, 11.9 g, 48.9 mmol) in glacial acetic acid (457 mL) at 60° C. After an additional 3 h, the reaction mixture was cooled to ambient temperatures and concentrated. The residue was partitioned between water and ethyl acetate. The ethyl acetate layer was dried (MgSO$_4$) and concentrated to provide the title compound as a white solid (10.9 g, 81%): mp 190°–196° C.; NMR (DMSO, d$^6$): δ 12.78 (broad s, 1H, NH) 8.00 (m, 2H, ArH), 7.58 (t, J=8.9 Hz, 2H, ArH), 6.70 (s, 1H, CH); MS(CI): 276 (M+H, 100%); Anal. (C$_9$H$_6$FNO$_4$S$_2$): C,H,N.

By the procedure described in Example 11, the compounds of formula (V), Examples 12–14, were prepared from the appropriate 5-(arylsulfanyl)-thiazolidine-2,4-dione of formula (III).

EXAMPLE 12

5-(Toluene-4-sulfonyl)-thiazolidine-2,4-dione, (V)

Prepared from 5-(toluene-4-sulfanyl)-thiazolidine-2,4-dione, (III) of Example 1: mp 73°–75° C.

EXAMPLE 13

5-(Naphthalene-2-sulfonyl)-thiazolidine-2,4-dione, (V) (Known: Zask et al, *J. Med. Chem.* 1990, 33, 1418–1423).

EXAMPLE 14

5-(4-Chlorophenylsulfonyl)-thiazolidine-2,4-dione, (V)

Prepared from 5-(4-chlorophenylsulfanyl)-thiazolidine-2, 4-dione, (III) of Example 7: mp 143°–144.5° C.

EXAMPLE 15

5-(Benzenesulfonyl)-thiazolidine-2,4-dione, (V)

A solution of 5-(benzenesulfanyl)-thiazolidine-2,4-dione, [(III), Example 6, 10.0 g, 41.8 mmol] in methanol (105 mL) was added to a mechanically stirred suspension of oxone (51.4 g, 83.6 mmol) in water (210 mL) at 0° C. The suspension was immediately warmed to room temperature. After 3.5 h, the reaction was diluted with water (1.5 L) and the solid was filtered. The solid was washed with water and dried in vacuo to provide the title compound as a white solid (8.31 g, 73%): mp 130°–133° C.: NMR (CDCL$_3$): δ 8.07 (s, 1H, NH), 7.98 (d, J=7.2 Hz, 2H, ArH) 7.78 (t, J=7.5 Hz, 1H, ArH), 7.67 (t, J=8.1Hz, 2H, ArH), 5.44 (s, 1H CH); MS(EI): 225 (MI, 24%), 182 (18%), 153 (12%), 110 (100%). By the procedure described in Example 15, the compounds of formula (V), Examples 16-18, were prepared from the appropriate 5-(arylsulfanyl)-thiazolidine-2,4-dione of formula (III).

EXAMPLE 16

5-(4-Bromophenylsulfonyl)-thiazolidine-2,4-dione, (V)

Prepared from 5-(4-bromophenylsulfanyl)-thiazolidine-2, 4-dione, (III) of Example 8: mp 156.5°–158° C.

EXAMPLE 17

5-(4-Methoxynhenylsulfonyl)-thiazolidine-2,4-dione, (V)

Prepared from 5-(4-methoxyphenylsulfanyl)-thiazolidine-2,4-dione, (III) of Example 9: mp 93°–95° C.

EXAMPLE 18

5-(Toluene-3-sulfonyl)-thiazolidine-2,4-dione, (V)

Prepared from 5-(toluene-3-sulfanyl)-thiazolidine-2,4-dione, (III) of Example 10: mp 96°–100° C.

EXAMPLE 19

5-(Pyridine-2-sulfonyl)-thiazolidine-2,4-dione, (V)

m-Chloroperbenzoic acid (25.7 g, 146 mmol) was added portionwise over 30 min to a stirred suspension of 5-(pyridine-2-sulfanyl)-thiazolidine-2,4-dione [(III), Example 2, 15.0 g, 66.3 mmol) in chloroform (600 mL) at room temperature. After 18 h, more m-chloroperbenzoic acid (4.65 g, 26.4 mmol) was added and the reaction mixture was stirred an additional 6 h. The reaction mixture was cooled in an ice bath and the resultant solid (18.7 g) was filtered. A 10 g portion of the resultant solid was purified by flash chromatography (9:1 CH$_2$Cl$_2$: acetonitrile) to provide the title compound as a white solid (4.18 g, 46%): mp 129°–131° C.; NMR (DMSO, d $^6$): δ 12.00 (broad s, 1H, NH), 8.85 (d, J=4.0 Hz, 1H, PyrH), 8.23 (dd, J=6.1, 7.9 Hz, 1H, PyrH), 8.12 (d, J=7.9 Hz, 1H, PyrH), 7.85 (dd, J=4.0, 6.1 Hz, 1H, PyrH), 6.79 (s, 1H, CH); MS(EI): 258 (MI, 8%), 215 (55%), 123 (22%) 78 (100%).

EXAMPLE 20

5-(Quinoline-2-sulfonyl)-thiazolidine-2,4-dione, (V)

30% Aqueous hydrogen peroxide (10.7 mL, 104 mmol) was added dropwise to a stirred solution of 2-quinolinethiol [(II), 8. 0 g, 49.6 mmol] in 2.5% aqueous NaOH (229 mL) and ethanol (229 mL). After 1 h the reaction mixture was concentrated to provide a white solid (8.34 g) which contained mainly sodium-2-naphthalenesulfinate (formula IV). A 7.0 g portion of this compound (≦32.5 mmol) was added to a solution of 5-bromo-thiazolidine-2,4-dione (6.38 g, 32.5 mmol) in dry DMF (53 mL) and the resultant solution was stirred at room temperature for 4 h. The DMF was removed in vacuo and water (400 mL) was added to the residue. The water phase was extracted with ethyl acetate (2×400 mL) and the combined ethyl acetate phase was dried (brine) and concentrated. The crude product was flash chromatographed (gradient: 98:2 to 97:3 CH$_2$Cl$_2$: isopropanol) to provide the title compound as a yellow solid (1.1 g, 9%): mp 168°–169° C.; NMR (DMSO, d $^6$): δ 12.9 (broad s, 1H, NH), 8.85 (d, J=8.8 Hz, 1H, ArH), 8.24 (d, J=8.1 Hz, 1H, ArH), 8.16 (d, J=8.7 Hz, 2H, ArH), 8.02 (dd, J=6.9, 8.3 Hz, 1H, ArH), 7.89 (dd, J=6.9, 8.1 Hz, 1H, ArH), 6.95 (s, 1H, CH); MS(EI): 308 (MI, 10%), 265 (8%), 145 (18%), 129 (100%), 128 (75%); Anal. (C$_{12}$H$_8$N$_2$O$_4$S$_2$): C,H,N.

EXAMPLE 21

[3-(4-Chlorophenyl)-prop-2-ynyl]-bromide, (IX)

A suspension of p-iodochlorobenzene [formula (VII), 7.15 g, 30.0 mmol], propargyl alcohol (1.75 mL, 30 mmol), dichlorobis(triphenylphosphine)palladium (II) (0.21 g, 0.3 mmol), copper (I) iodide (29 mg, 0.15 mmol) and diethylamine (50 mL) was stirred under a N$_2$ atmosphere at room temperature and dissolution occurred within 20 min. After 5 h, the diethylamine was removed, and the crude product was partitioned between water and ether. The ether phase was dried (brine), concentrated and flash chromatographed (4:1 petroleum ether: ethyl acetate) to provide 3-(4-chlorophenyl)-prop-2-yn-ol (compound of formula VIII, 4.09 g, 82%). This compound of formula (VIII) ( 3.47 g, 20.83 mmol) was suspended in dry ether (12 mL) and pyridine (0.42 mL) was added. The reaction mixture was cooled in an ice bath and a solution of phosphorus tribromide (1.0 mL, 10.42 mmol) in dry ether (6 mL) was added dropwise over a 15 min period. The reaction mixture was then stirred at room temperature for 2.5 h, cooled in an ice bath and crushed ice was added. The reaction mixture was added to water (200 mL) and extracted with ether (200 mL). The ether phase was washed with water, sat. aqueous NaHCO$_3$ and brine. The extract was concentrated and flash chromatographed (9:1 petroleum ether:ethyl acetate) to provide the product as a white solid (3.38 g, 86%): mp 41°–43 ° C.; NMR (CDCl$_3$): δ 7.37 (d, J=8.7 Hz, 2H, ArH), 7.27 (d, J=8.7 Hz, 2H, Ar H), 4.16 (s, 2H, CH$_2$).

By the procedure described in Example 21, the compounds of formula (IX), Examples 22-33, were prepared from the appropriate, commercially available aryliodide of formula (VII) or comercially available 3-arylprop-2-yn-ol of formula (VIII).

EXAMPLE 22

[3-Benzene-prop-2-ynyl]-bromide, (IX)

Prepared from 3-benzene-prop-2-yn-ol, (VIII): oil, NMR (CDCl$_3$) δ 7.43 (m, 2H, ArH), 7.33 (m, 3H, ArH), 4.16 (s, 2H, CH$_2$).

EXAMPLE 23

[3-[4-(Fluorophenyl)]-prop-2-ynyl]-bromide, (IX)

Prepared from p-fluoroiodobenzene, (VII): oil; MS(E1): 212 (MI, 8%), 214 (MI, 8%), 133 (100%).

EXAMPLE 24

[3-[4-(Methylphenyl)]-prop-2-ynyl]-bromide, (IX)

Prepared from p-methyliodobenzene, (VII): oil; MS(EI): 208 (MI, 8%), 210 (MI, 8%), 129 (100%).

EXAMPLE 25

[3-[4-(Trifluoromethylphenyl)]-prop-2-ynyl]-bromide, (IX)

Prepared from p-iodo(trifluoromethyl)benzene, (VII): oil; NMR (CDCl$_3$): δ 7.57 (d, J =8.6 Hz, 2H, ArH), 7.52 (d, J=8.6 Hz, 2H, ArH), 4.13 (s, 2H, CH$_2$).

EXAMPLE 26

[3-[4-(Bromophenyl)]-prop-2-ynyl]-bromide, (IX)

Prepared from p-bromoiodobenzene, (VII): mp 50°–51° C.

EXAMPLE 27

[3-[4-(Methoxyphenyl)]-prop-2-ynyl]-bromide (IX)

Prepared from p-iodoanisole, (VII): oil; NMR (CDCl$_3$): δ 7.37 (d, J=8.8 Hz, 2H, ArH), 6.83 (d, J=8.8 Hz, 2H, Ar H), 4.16 (s, 2H, CH$_2$), 3.80 (s, 3H, CH$_3$).

EXAMPLE 28

[3-[4-(Trifluoromethoxyhenyl)]-prop-2-ynyl]-bromide, (IX)

Prepared from p-trifluoromethoxyiodobenzene, (VII): oil; NMR (DMSO, d$^6$): δ 7.58 (d, J=8.8 Hz, 2H, ArH), 7.37 (d, J=8.8 Hz, 2H, ArH), 4.49 (s, 2H, CH$_2$).

EXAMPLE 29

[3-[3-(Chlorophenyl)]l-prop-2-ynvl]-bromide, (IX)

Prepared from m-chloroiodobenzene, (VII): oil; NMR (CDCl$_3$): δ 7.44 (s, 1H, ArH), 7.32 (m, 2H, ArH), 7.28 (m, 2H, ArH), 4.14 (s, 2H, CH$_2$).

EXAMPLE 30

[3-[2-(Chlorophenyl)]-prop-2-ynyl]-bromide, (IX)

Prepared from o-chloroiodobenzene, (VII): oil; NMR (CDCl$_3$): δ 7.48 (dd, J=1.9, 7.3 Hz, 1H, ArH), 7.40 (dd, J=1.5, 8.1 Hz, 1H, ArH), 7.25 (m, 2H, ArH), 4.21 (s, 2H, CH$_2$).

EXAMPLE 31

[3-(3,5-bis(trifluoromethyl)phenyl)-prop-2-ynyl]-bromide, (IX)

Prepared from 3-[3, 5-bis(trifluoromethyl)phenyl]-prop-2-yn-ol, (VIII): mp 30°–31° C.

EXAMPLE 32

[3-[4-(Methylthiophenyl)]-prop-2-ynyl]-bromide, (IX)

Prepared from p-iodothioanisole, (VII): oil; NMR (DMSO, d$^6$): δ 7.36 (d, J=8.3 Hz, 2H, ArH), 7.22 (d, J=8.3 Hz, 2H, ArH), 4.48 (s, 2H, CH$_2$).

EXAMPLE 33

[3-(3,5-Bis(fluoro)phenyl)-prop-2-ynyl]-bromide (IX)

Prepared from 3, 4-difluoroiodobenzene, (VII): oil; MS(EI): 231 (MI, 16%), 233 (MI, 16%), 151 (100%).

EXAMPLE 4

N-(Triphenylmethyl)-5-(toluene-4-sulfonyl)-thiazolidine-2,4-dione, (VI)

Triphenylmethyl chloride (2.67 g, 9.58 mmol) was added to a stirred, room temperature solution of 5-(toluene-4-sulfonyl)-thiazolidine-2,4-dione [(V), from Example 12, 1.30 g, 4.79 mmol], triethylamine (0.67 mL, 4.79 mmol) and dichloromethane (6.5 mL). After 1h, water (300 mL) was added and the organic material was extracted with ethyl acetate (2×200 mL). The combined extracts were dried (brine, MgSO$_4$), concentrated and purified by flash chromatography (4:1 petroleum ether:ethyl acetate) to provide the title compound as a white solid (1.1 g, 45%): mp 105°–110° C.; NMR (CDCl$_3$): δ 7.85 (d, J=8.3 Hz, 2H, ArH), 7.48 (d, J=8.1 Hz, 6H, CPh$_3$H), 7.38 (d, J=8.3 Hz, 2H, ArH),7.23 (m, 9H, CPh$_3$H), 5.13 (s, 1H, CH), 2.46 (s, 3H, CH$_3$).

EXAMPLE 35

N-(Triphenylmethyl)-5-[3-(4-chlorophenyl)-prop-2-ynyl]-5-(toluene-4-sulfonyl)-thiazolidine-2,4-dione, (X)

Sodium hydride (80% dispersion in mineral oil, 93 mg, 3.10 mmol) was added to a solution of N-(triphenylmethyl)-5-(toluene-4-sulfonyl)-thiazolidine-2,4-dione [(VI), from Example 34, 1.06 g, 2.07 retool) in dry DMF (9 mL) at 0° C. under a dry N$_2$ atmosphere. After 20 min, [3-(4-chlorophenyl)-prop-2-ynyl]-bromide [(IX), from Example 21, 0.52 g, 2.27 mmol] was added and the reaction mixture was stirred an additional 20 min at 0° C. Saturated aqueous NH$_4$Cl$_1$ (60 mL) was added, followed by water (60 mL). After stirring for 10 min, the solid was filtered, washed with water and triturated with petroleum ether to provide the title compound as a grey solid (1.16 g, 0%): mp 221°–223° C.; NMR (CDCl$_3$): δ 7.80 (d, J=8.2 Hz, 2H, ArH), 7.45 (d, J=7.5 Hz, 6H, CPh$_3$H), 7.35 (d, J=8.2 Hz, 2H, ArH), 7.14 (m, 11H, Ar'H, CPh$_3$H) 6.98 (d, J=8.5 Hz, 2H, Ar'H), 3.29 (d, J=16.7 Hz, 1H, CH$_2$), 3.12 (d, J=16.7 Hz, 1H, CH$_2$), 2.46 (s, 3H, CH$_3$).

EXAMPLE 36

5-[3-(4-Chlorophenyl)-prop-2-ynyl]-5-(toluene-4-sulfonyl)-thiazolidine-2,4-dione, (I)

Trifluoroacetic acid (0.32 mL, 4.07 mmol) was added to a room temperature, stirred suspension of N-(triphenylmethyl)-5-[3-(4-chlorophenyl)-prop-2-ynyl]-5-(toluene-4-sulfonyl)-thiazolidine-2,4-dione [(X), from Example 35, 1.29 g, 1.94 mmol] in CH$_2$Cl$_2$ (2 mL). Dissolution occurred immediately. After 1 h, the reaction mixture was added to water (200 mL) and extracted with ethyl acetate (200 mL). The ethyl acetate phase was washed with water and brine and then concentrated. The crude product was purified by flash chromatography (95:5 CH$_2$Cl$_2$:isopropanol) and then triturated in petroleum ether to provide the title compound as a off-white solid (0.52 g, 64%): mp 172°–174° C.; NMR (CDCl$_3$): δ 8.00 (s, 1H, NH) 7.85 (d, J=8.3 Hz, 2H, Ar H), 7.41 (d, J=8.3 Hz, 2H, ArH), 7.26 (s, 4H, Ar'H), 3.65 (d, J=17.1 Hz, 1H, CH$_2$), 3.33 (d, J=17.1 Hz, 1H, CH$_2$), 2.49 (s, 3H, CH$_3$); MS(CI); 420 (M+H,58%), 422 (M+H, 24%), 265 (40%), 267 (26%),157 (100%); Anal. Calc. for C$_{19}$H$_{14}$ClNO$_4$S$_2$: C, 54.35; H, 3.36; N, 3.36; Found: C, 54.74; H, 3.54; N, 2.98.

EXAMPLE 37

5-[3-(4-Chlorophenyl)-prop-2-ynyl]-5-(toluene-4-sulfanyl)-thiazolidine-2,4-dione, (I)

Sodium hydride (80% dispersion in mineral oil, 0.63 g, 21.1 mmol) was added to a solution of 5-(toluene-4-sulfanyl)-thiazolidine-2,4-dione [(III), from Example 1, 1.75 g, 8.44 mmol] in dry THF (9 mL) at 0° C. under a dry N$_2$ atmosphere. After 10 min, a solution of [3-(4-chlorophenyl)-prop-2-ynyl]-bromide [(IX), from Example 21, 1.94 g, 8.44 mmol] in dry THF (9 mL) was added over a 30 min period. After 2.5 h, the reaction mixture was concentrated and dilute aqueous HCl was added (85 mL). The organics were extracted with ethyl acetate (2×85 mL) and the extracts were dried (brine), concentrated, purified by flash chromatography (98:2 CH$_2$Cl$_2$:isopropanol) and triturated with petroleum ether to provide the title compound as a white solid (1.25 g, 38%): mp 108°–109° C.: NMR (DMSO, d $^6$): δ 12.27 (s, 1H, NH), 7.46 (d, J=8.5 Hz, 2H, ArH, Ar'H), 7.39 (d, J=8.7 Hz, 1H, Ar'HH), 7.27 (d, J=7;9 Hz, 1H, ArH), 3.48 (d, J=17.3 Hz, 1H, CH$_2$), 3.32 (d, J=17.3 Hz, 1H, CH$_2$), 2.34 (s, 3H, CH$_3$); MS(EI): 387 (MI, 5%), 389 (2%), 124 (85%), 91 (100%); Anal. Calc. for C$_{19}$H$_{14}$ClNO$_2$S$_2$: C, 58.21; H, 3.53; N, 3.77; Found: C, 58.02; H, 3.58; N, 3.52.

Using the procedure described in Example 37, the compounds of formula (I), Examples 38–41, were prepared from the appropriate 5-arylsulfanyl-thiazolidine-2,4-dione of formula (III) and the appropriate (3-arylprop-2-ynyl)-bromide of formula (IX).

EXAMPLE 38

5-[3-(4-Chlorophenyl)-prop-2-ynyl]-1-5-benzenesulfanyl-thiazolidine-2,4-dione, (I)

Prepared from 5-(benzenesulfanyl)-thiazolidine-2,4-dione of formula (III), Example 6 and [3-(4-chlorophenyl)-prop-2-ynyl]-bromide of formula (IX), from Example 21: mp 87°–88° C.; Anal. Calc. for C$_{18}$H$_{12}$ClNO$_2$S$_2$: C, 57.83; H, 3.24; N, 3.75; Found: C, 58.05; H, 3.07; N, 3.62.

EXAMPLE 39

5-[3-(4-Chlorophenyl)prop-2-ynyl]-5-(4-fluorophenyl-sulfanyl)-thiazolidine-2,4-dione, (I)

Prepared from 5-(4-fluorophenyl-sulfanyl)-thiazolidine-2,4-dione of formula (III), Example 5 and [3-(4-chlorophenyl)-prop-2-ynyl]-bromide of formula (IX), from Example 21: mp 116°–117° C.; Anal. Calc. for C$_{18}$H$_{11}$ClFNO$_2$S$_2$: C, 55.17; H, 2.83; N, 3.57; Found: C, 54.58; H, 2.65; N, 3.39.

EXAMPLE 40

5-[3-(4-Chlorophenyl)-prop-2-ynyl]-5-(pyridine-2-sulfanyl)-thiazolidine-2,4-dione, (I)

Prepared from 5-(pyridine-2-sulfanyl)-thiazolidine-2,4-dione, (III) from Example 2 and [3-(4-chlorophenyl)-prop-2-ynyl]-bromide of formula (IX), from Example 21: mp 124°–125° C.; Anal. Calc. for C$_{17}$H$_{11}$ClN$_2$O$_2$S$_2$: C, 54.47; H, 2.96; N, 7.47; Found: C, 54.49; H, 2.86; N, 7.14.

EXAMPLE 41

5-[3-(4-Chlorophenyl)-prop-2-ynyl]-5-(quinoline-2-sulfanyl)-thiazolidine-2,4-dione, (I)

Prepared from 5-(quinoline-2-sulfanyl)-thiazolidine-2,4-dione, (III) from Example 3 and [3-(4-chlorophenyl)-prop-2-ynyl]-bromide of formula (IX), from Example 21: mp 163°–165° C.; Anal. Calc. for C$_{21}$H$_{13}$ClN$_2$O$_2$S$_2$: C, 58.04; H, 3.06 N, 6.40; Found: C, 57.98; H, 2.84; N, 6.15.

EXAMPLE 42

5-[3-(4-Chlorophenyl)-prop-2-ynyl]-5-(4-fluorobenzenesulfonyl)-thiazolidine-2,4-dione, (I)

Sodium hydride (80% dispersion in mineral oil, 0.55 g, 18.2 mmol) was added to a solution of 5-(4-fluorophenyl-sulfonyl)-thiazolidine-2,4-dione [(V), from Example 11, 2.0 g, 7.27 mmol] in dry THF (12 mL) at 0° C. under a dry N$_2$ atmosphere. After 1.5 h, a solution of [3-(4-chlorophenyl)-prop-2-ynyl]-bromide [(IX), from Example 21, 1.67 g, 7.27 mmol] in dry THF (12 mL) was added over a 25 min period. After 20 h, the reaction mixture was concentrated and dilute aqueous HCl was added (100 mL). The organics were extracted with ethyl acetate (3×100 mL) and the extracts were dried (brine), concentrated, purified by flash chromatography (97:3 CH$_2$Cl$_2$:methanol) and triturated with petroleum ether to provide the title compound as a white solid (0.99 g, The solid was further purified by recrystallization from ethanol:water: mp 176°–177° C.; NMR (DMSO, d $^6$): δ 13.0 (broad s, 1H, NH), 8.02 (m, 1H, ArH), 7.59 (t, J=8.9 Hz, 1H, ArH), 7.45 (d, J=8.5 Hz, 1H, Ar'H), 7.35 (d, J=8.5 Hz, 1H Ar'H), 3.66 (d, J=17.5 Hz, 1H, CH$_2$), 3.50 (d, J=17.3 Hz, 1H, CH$_2$); MS(–DCI): 422 (M–H, 22%), 424 (M–H, 16%), 263 (100%), 265 (40%); Anal. Cala. for C$_{18}$H$_{11}$ClFNO$_4$S$_2$: C, 51.01; H, 2.62; N, 3.30; Found: C, 51.08; H, 2.55; N, 2.97.

EXAMPLE 43

5-[3-(4-Chlorophenyl)-prop-2-ynvl]-5-(pyridine-2-sulfonyl)-thiazolidine-2,4-dione, (I)

Sodium hydride (80% dispersion in mineral oil, 0.32 g, 10.8 mmol) was added to a solution of 5-(pyridine-2-sulfonyl)-thiazolidine-2,4-dione [(V), from Example 19, 1.1 g, 4.30 mmol] in dry THF (7.5 mL) at 0° C. under a dry N$_2$ atmosphere. After 10 min, a solution of [3-(4-chlorophenyl)-prop-2-ynyl]-bromide [(IX), from Example 21, 0.99 g, 4.30 mmol] in dry THF (7.5 mL) was added over a 30 min period. After 27 h at room temperature, the reaction mixture was quenched with saturated aqueous NH$_4$Cl (20mL), water (120 mL) was added and the organics were extracted with ethyl acetate (2×150 mL).The extracts were dried (brine), concentrated and purified by flash chromatography (gradient: 97:3 to 88:12 CH$_2$Cl$_2$:methanol) to provide the title compound as a yellow solid (0.63 g, 36%): mp 140°–141°

C.; NMR (DMSO, d $^6$): δ 13.2 (broad s, 1H, N$\underline{H}$), 8.82 (dd, J=0.6, 4.0 Hz, 1H, Pyr$\underline{H}$), 8.23 (td, J=1.6, 7.8 Hz, 1H, Pyr $\underline{H}$), 8.15 (d, J=7.9 Hz, 1H, Pyr$\underline{H}$), 7.87 (ddd, J=1.1, 5.3, 7.7 Hz, 1H, Pyr$\underline{H}$), 7.45 (d, J=8.5 Hz, 1H, Ar'$\underline{H}$), 7.35 (d, J=8.5 Hz, 1H, Ar'$\underline{H}$), 3.88 (d, J=17.2 Hz, 1H, C$\underline{H}_2$), 3.74 (d, J=17.2 Hz, 1H, C$\underline{H}_2$); MS(+DCI): 407 (M+H, 50%), 409 (M+H, 24%), 264 (80%), 266 (36%), 144 (100%); Anal. Calc. for $C_{17}H_{11}ClN_2O_4S_2$: C, 50.18; H, 2.72; N, 6.88; Found: C, 50.07; H, 2.67; N, 6.57.

By the procedure described in Example 43, the compounds of formula (I), Examples 44–85, were prepared from the appropriate 5-arylsulfonyl-thiazolidine-2,4-dione of formula (V) and the appropriate (3-arylprop-2-ynyl)-bromide of formula (IX).

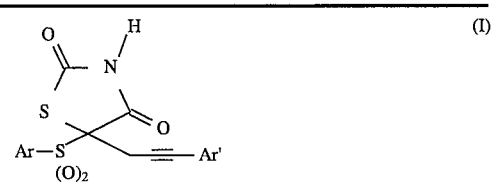
(I)

| Example | Ar | Ar¹ | Examples of Starting Materials | Analysis Calc. C, H, N Found C, H, N | mp (°C.) |
|---|---|---|---|---|---|
| 44 | 2-naphthyl | 4-chloro-phenyl | 13 and 21 | $C_{22}H_{14}ClNO_4S_2$ 57.95, 3.09, 3.07 57.70, 3.09, 2.97 | 190–191 |
| 45 | phenyl | 4-chloro-phenyl | 15 and 21 | $C_{18}H_{12}ClNO_4S_2$ 53.27, 2.98, 3.45 52.99, 3.13, 3.31 | 92–93 |
| 46 | phenyl | phenyl | 15 and 22 | $C_{18}H_{13}NO_4S_2$ 58.21, 3.53, 3.77 58.02, 3.58, 3.52 | 130–131 |
| 47 | 4-methyl-phenyl | phenyl | 12 and 22 | $C_{19}H_{15}NO_4S_2$ 59.20, 3.92, 3.63 59.01, 3.96, 3.30 | 143–145 |
| 48 | 4-chloro-phenyl | phenyl | 14 and 22 | $C_{18}H_{12}ClNO_4S_2$ 53.27, 2.98, 3.45 53.25, 2.87, 3.25 | 144–146 |
| 49 | 4-chloro-phenyl | 4-chloro-phenyl | 14 and 21 | $C_{18}H_{11}Cl_2NO_4S_2$ 49.10, 2.52, 3.18 49.25, 2.40, 3.02 | 172–173 |
| 50 | 4-fluoro-phenyl | phenyl | 11 and 22 | $C_{18}H_{12}FNO_4S_2$ 55.52, 3.11, 3.60 55.37, 3.04, 3.32 | 135–141 |
| 51 | 4-bromo-phenyl | 4-chloro-phenyl | 16 and 21 | $C_{18}H_{11}BrClNO_4S_2$ 44.60, 2.29, 2.89 44.31, 2.20, 2.70 | 171–175 |
| 52 | phenyl | 4-fluoro-phenyl | 15 and 23 | $C_{18}H_{12}FNO_4S_2$ 55.52, 3.11, 3.60 55.14, 2.98, 3.37 | 171–172 |
| 53 | 4-methyl-phenyl | 4-fluoro-phenyl | 12 and 23 | $C_{19}H_{14}FNO_4S_2$ 56.56, 3.50, 3.47 55.83, 3.38, 3.17 | 154–156 |
| 54 | phenyl | 4-methyl-phenyl | 15 and 24 | $C_{19}H_{15}NO_4S_2$ 59.20, 3.92, 3.63 58.85, 3.81, 3.56 | 168–169 |
| 55 | 4-methyl-phenyl | 4-methyl-phenyl | 12 and 24 | $C_{20}H_{17}NO_4S_2$ 60.13, 4.29, 3.51 60.07, 4.25, 3.47 | 195–196 |
| 56 | 4-bromo-phenyl | phenyl | 16 and 22 | $C_{18}H_{12}BrNO_4S_2$ 48.01, 2.69, 3.11 47.87, 2.55, 3.11 | 172–176 |
| 57 | 4-methoxy-phenyl | 4-chloro-phenyl | 17 and 21 | $C_{19}H_{14}ClNO_5S_2$ 52.35, 3.24, 3.21 52.21, 3.17, 3.03 | 134–136 |
| 58 | 2-napthyl- | phenyl | 13 and 22 | $C_{22}H_{15}NO_4S_2$ 62.69, 3.58, 3.32 62.40, 3.53, 3.37 | 174–177 |
| 59 | 4-methoxy-phenyl | phenyl | 17 and 22 | $C_{19}H_{15}NO_5S_2$ 56.84, 3.77, 3.49 56.81, 3.68, 3.32 | 142–143 |
| 60 | 4-methyl-phenyl | 4-trifluoro-methyl-phenyl | 12 and 25 | $C_{10}H_{14}F_3NO_4S_2$ 52.98, 3.11, 3.09 52.60, 3.04, 2.94 | 78–80 |
| 61 | phenyl | 4-bromo-phenyl | 15 and 26 | $C_{18}H_{12}BrNO_4S_2$ 48.01, 2.69, 3.11 47.72, 2.54, 2.72 | 81–83 |
| 62 | 4-methoxy-phenyl | 4-methoxy-phenyl | 12 and 27 | $C_{20}H_{17}NO_5S_2$ 57.82, 4.12, 3.37 57.12, 4.05, 2.87 | 80–82 |

-continued

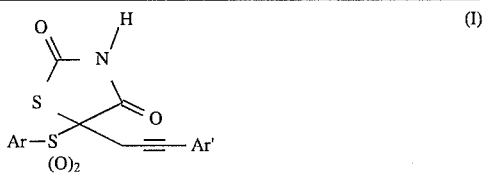

| Example | Ar | Ar¹ | Examples of Starting Materials | Analysis Calc. C, H, N Found C, H, N | mp (°C.) |
|---|---|---|---|---|---|
| 63 | 4-methyl-phenyl | 4-bromo-phenyl | 12 and 26 | $C_{19}H_{14}BrNO_4S_2$<br>49.14, 3.04, 3.02<br>49.10, 2.84, 2.72 | 161–162 |
| 64 | 3-methyl-phenyl | phenyl | 18 and 22 | $C_{19}H_{15}NO_4S_2$<br>54.35, 3.36, 3.34<br>54.27, 3.20, 3.02 | 128–130 |
| 65 | phenyl | 4-trifluoro-methyl-phenyl | 15 and 25 | $C_{19}H_{12}F_3NO_4S_2 \cdot 0.53H_2O$<br>51.93, 2.75, 3.18<br>50.62, 2.76, 3.06 | 80–81 |
| 66 | 4-fluoro-phenyl | 4-fluoro-phenyl | 11 and 23 | $C_{18}H_{11}F_2NO_4S_2$<br>53.07, 2.72, 3.44<br>53.05, 2.69, 3.27 | 177–181 |
| 67 | 4-chloro-phenyl | 4-fluoro-phenyl | 14 and 23 | $C_{18}H_{11}ClFNO_4S_2$<br>51.00, 2.62, 3.30<br>50.83, 2.59, 3.07 | 171–173 |
| 68 | 3-methyl-phenyl | 4-chloro-phenyl | 18 and 21 | $C_{19}H_{15}ClNO_4S_2$<br>54.35, 3.36, 3.34<br>54.27, 3.20, 3.02 | 136–137.5 |
| 69 | 4-methyl-phenyl | 3-chloro-phenyl | 12 and 29 | $C_{19}H_{14}ClNO_4S_2$<br>54.35, 3.36, 3.34<br>53.94, 3.20, 3.04 | 70–72 |
| 70 | phenyl | 4-methoxy-phenyl | 15 and 27 | $C_{19}H_{15}NO_5S_2 \cdot 0.71H_2O$<br>55.09, 4.00, 3.38<br>54.78, 3.73, 3.09 | 161–162 |
| 71 | phenyl | 2-chloro-phenyl | 15 and 30 | $C_{18}H_{12}ClNO_4S_2$<br>53.27, 2.98, 3.45<br>53.09, 2.82, 3.32 | 162–163 |
| 72 | 4-methyl-phenyl | 2-chloro-phenyl | 12 and 30 | $C_{19}H_{14}ClNO_4S_2$<br>54.35, 3.36, 3.34<br>54.00, 3.20, 3.32 | 160–161 |
| 73 | phenyl | 3,5-bis-trifluoro-methyl-phenyl | 15 and 31 | $C_{20}H_{11}F_6NO_4S_2$<br>47.34, 2.19, 2.76<br>47.10, 2.02, 2.73 | 226–229 |
| 74 | 4-methyl-phenyl | 3,5-bis-trifluoro-methyl-phenyl | 12 and 31 | $C_{21}H_{13}F_6NO_4S_2$<br>48.37, 2.51, 2.69<br>48.24, 2.29, 2.53 | 207–209 |
| 75 | phenyl | 3-chloro-phenyl | 15 and 29 | $C_{18}H_{12}ClNO_4S_2$<br>53.27, 2.98, 3.45<br>53.03, 2.81, 3.37 | 107–108 |
| 76 | 4-fluoro-phenyl | 4-bromo-phenyl | 11 and 26 | $C_{18}H_{11}BrFNO_4S_2$<br>46.16, 2.37, 2.99<br>46.26, 2.24, 2.75 | 155–157 |
| 77 | 4-chloro-phenyl | 4-bromo-phenyl | 14 and 26 | $C_{18}H_{11}BrClNO_4S_2$<br>44.59, 2.28, 2.89<br>44.27, 2.17, 2.65 | 160–161 |
| 78 | 4-fluoro-phenyl | 4-trifluoro-methyl-phenyl | 11 and 25 | $C_{19}H_{11}F_4NO_4S_2$<br>49.89, 2.42, 3.06<br>49.90, 2.37, 3.04 | 143–145 |
| 79 | 4-chloro-phenyl | 4-trifluoro-methyl-phenyl | 14 and 25 | $C_{19}H_{11}ClF_3NO_4S_2$<br>48.16, 2.34, 2.95<br>47.91, 2.46, 2.85 | 144–145 |
| 80 | 4-bromo-phenyl | 4-fluoro-phenyl | 16 and 23 | $C_{18}H_{11}BrFNO_4S_2$<br>46.16, 2.36, 3.00<br>45.13, 2.42, 2.81 | 186–188 |
| 81 | 2-pyridyl | 4-fluoro-phenyl | 19 and 23 | $C_{17}H_{11}FN_2O_4S_2$<br>52.30, 2.84, 7.18<br>52.05, 2.71, 2.09 | 92–94 |
| 82 | 4-fluoro-phenyl | 4-trifluoro-methoxy-phenyl | 11 and 28 | $C_{19}H_{11}F_4NO_5S_2$<br>48.20, 2.34, 2.96<br>48.40, 2.48, 2.90 | 133–135 |
| 83 | 4-fluoro-phenyl | 3,4-di-fluoro-phenyl | 11 and 33 | $C_{18}H_{10}F_3NO_4S_2$<br>50.82, 2.37, 3.29<br>49.83, 2.39, 3.44 | 130–133 |

$$\text{(I)}$$

Structure: Ar—S(O)₂—C(S—...)(—C(=O)—N(H)—C(=O)—)—Ar' with thiazolidine-2,4-dione ring

| Example | Ar | Ar¹ | Examples of Starting Materials | Analysis Calc. C, H, N Found C, H, N | mp (°C.) |
|---|---|---|---|---|---|
| 84 | 4-fluoro-phenyl | 4-methyl-thio-phenyl | 11 and 32 | $C_{19}H_{14}FNO_4S_3$ 52.40, 3.24, 3.22 52.41, 3.31, 2.82 | 74–76 |
| 85 | 2-quinolyl | 4-chloro-phenyl | 20 and 21 | $C_{21}H_{13}ClN_2O_4S_2$ 55.20, 2.87, 6.13 55.08, 2.67, 6.28 | 191–192 |

EXAMPLE 86

5-(6-Methyl-pyridine-2-sulfanyl)-thiazolidine-2,4-dione, (III)

This compound was prepared from 5-bromo-thiazolidine-2,4-dione and 2-methyl-6-mercaptopyridine (A. D. Dunn, R. Norrie, J. L'Hostis, and S. Marjot J. Prak. Chem.—Chem. Zt. 1992, 334, 119–125) according to the procedure described in Example 1: mp 114–115.

EXAMPLE 87

5-(Pyrimidine-2-sulfanyl)-thiazolidine-2,4-dione, (III)

This compound was prepared from 5-bromo-thiazolidine-2,4-dione and 2-mercaptopyrimidine according to the procedure described in Example 1: MS(EI): 227 (MI,5%), 184 (15%), 80 (100%).

EXAMPLE 88

5-(5-Chloro-benzothiazol-2-ylsulfanyl)-thiazolidine-2,4-dione, (III)

This compound was prepared from 5-bromo-thiazolidine-2,4-dione and 5-chloro-2-mercaptobenzothiazole according to the procedure described in Example 5: mp 253–255 (dec).

EXAMPLE 89

5-(Benzoxazol-2-ylsulfanyl)-thiazolidine-2,4-dione, (III)

This compound was prepared from 5-bromo-thiazolidine-2,4-dione and 2-mercaptobenzoxazole according to the procedure described in Example 5: mp 241–243 (dec).

EXAMPLE 90

5-(6-Methyl-pyridine-2-sulfonyl)-thiazolidine-2,4-dione, (IV)

This compound was prepared from 5-bromo-thiazolidine-2,4-dione and 2-methyl-6-mercaptopyridine (A. D. Dunn, R. Norrie, J. L'Hostis, and S. Marjot J. Prak. Chem.—Chem. Zt. 1992, 334, 119–125) according to the procedure described in Example 20: mp 129–130 (dec).

EXAMPLE 91

5-[3-(4-Chlorophenyl)-prop-2-ynyl]-5-(4-chlorophenylsulfanyl)-thiazolidine-2,4-dione, (I)

N-butyl lithium (2.5 M in hexanes, 12.3 mL, 30.8 mmol) was added to a solution of 5-(4-chlorophenylsulfanyl)-thiazolidine-2,4-dione [(III), from Example 7, 4.0 g, 15.4 mmol] in dry THF (195 mL) at −78° C. under a dry N2 atmosphere over a forty minute period. After an additional 30 min, a solution of [3-(4-chlorophenyl)-prop-2-ynyl]-bromide [(IX), from Example 21, 3.53 g, 15.4 mmol] in dry THF (65 mL) was added over a 12 min period. After 10 min, the reaction mixture was allowed to warm to room temperature. After 2 h, the reaction mixture was added to saturated aqueous ammonium chloride (1 L) and extracted with ethyl acetate (800 mL). The extracts were dried (brine), concentrated and purified by flash chromatography (4:1 petroleum ether:ethyl acetate) to provide the title compound as a white solid (2.58 g, 41%): mp 144°–146° C.: NMR (DMSO, d⁶): δ 12.37 (s, 1H, NH), 7.59 (d, J=8.5 Hz 2H, ArH), 7.56 (d, J=8.7 Hz, 2H, ArH), 7.46 (d, J=8.5 Hz, 2H, Ar'H), 7.40 (d, J=8.3 Hz, 2H, Ar'H), 3.52 (d, J=17.3 Hz, 1H, CH₂), 3.35 (d, J=17.3 Hz, 1H, CH₂); MS(EI): 407, 409, 411 (MI, 5%), 364, 366 (8%), 264 (30%), 193 (40%), 149 (100%), 143 (20%); Anal. Calc. for $C_{18}H_{11}Cl_2NO_2S_2$: C, 52.95; H, 2.72; N, 3.43; Found: C, 52.95; H, 2.87; N, 3.29.

Using the procedure described in Example 91, the compounds of formula (I), Examples 92–95, were prepared from the appropriate 5-arylsulfanyl-thiazolidine-2,4-dione of formula (III) and [3-(4-chlorophenyl)-prop-2-ynyl]-bromide of formula (IX), Example 21.

EXAMPLE 92

5-(5-Chlorobenzothiazol-2-ylsulfanyl)-5-[3-(4-chlorophenyl-prop-2-ynyl-thiazolidine-2,4-dione, (I)

Prepared from 5-(5-chloro-benzothiazol-2-ylsulfanyl)-thiazolidine-2,4-dione, (III), Example 88 and [3-(4-chlorophenyl)-prop-2-ynyl]-bromide of formula (IX), Example 21: mp 187°–188° C.; Anal. Calc. for $C_{19}H_{10}Cl_2N_2O_2S_3$: C, 49.04; H, 2.17; N, 6.02; Found: C, 48.94; H, 2.31; N, 6.21.

EXAMPLE 93

5-(Benzoxazol-2-ylsulfanyl)-5-[3-(4-chlorophenyl)-prop-2-ynyl]-thiazolidine-2,4-dione, Prepared from 5-(benzoxazol-2-ylsulfanyl)-thiazolidine-2,4-dione, (III), Example 89 and [3-(4-chlorophenyl)-prop- 2-ynyl]-bromide of formula (IX), Example mp 137°–139° C.; Anal. Calc. for $C_{19}H_{11}ClN_2O_3S_2$: C, 55.80; H, 2.67; N, 6.75; Found: C, 54.92; H, 2.76; N, 6.82.

EXAMPLE 4

5-[3-(4-Chlorophenyl)-prop-2-ynyl]-5-(6-methyl-pyridine-2-sulfanyl)-thiazolidine-2,4-dione, (I)

Prepared from 5-(6-Methyl-pyridine-2-sulfanyl)-thiazolidine-2,4-dione, (III), Example 86 and [3-(4-chlorophenyl)-prop-2-ynyl]-bromide of formula (IX), Example mp 147°–148° C.; Anal. Calc. for $C_{18}H_{13}ClN_2O_2S_2$: C, 55.59; H, 3.37; N, 7.20; Found: C, 55.52; H, 3.31; N, 7.02.

EXAMPLE 95

5-[3-(4-Chlorophenyl)-prop-2-ynyl]-5-(pyrimidine-2-sulfanyl)-thiazolidine-2,4-dione, Prepared from 5-(pyrimidine-2-sulfanyl)-thiazolidine-2,4-dione, (III), Example 87 and [3-(4-chlorophenyl)-prop-2-ynyl]-bromide of formula (IX), Example 21: mp 118°–120° C.; Anal. Calc. for $C_{16}H_{10}ClN_3O_2S_2$: C, 51.13; H, 2.68; N, 11.18; Found: C, 51.27; H, 2.93; N, 10.82.

EXAMPLE 96

5-[3-(4-Chlorophenyl)-prop-2-ynyl]-5-(6-methyl-pyridine-2-sulfonyl)-thiazolidine-2,4-dione, (I)

N-butyl lithium (2.5 M in hexanes, 2.77 mL, 6.93 mmol) was added to a solution of 5-(6-methyl-pyridine-2-sulfonyl)-thiazolidine-2,4-dione, [(V), from Example 90, 0.92 g, 3.38 mmol] in dry THF (30 mL) at –78° C. under a dry $N_2$ atmosphere over a twenty minute period. A solution of [3-(4-chlorophenyl)-prop-2ynyl]-bromide [(IX), from Example 21, 3.53 g, 15.4 mmol] in dry THF (10 mL) was added over a 20 rain period. The reaction mixture was allowed to warm to room temperature. After 16 h, the reaction mixture was added to saturated aqueous ammonium chloride (80 mL) and extracted with ethyl acetate (2×300 mL). The extracts were washed with water, dried (brine), concentrated and purified by flash chromatography (gradient 97:3 to 93:7 $CH_2Cl_2$: isopropanol) to provide a sticky solid which triturated with petroleum ether (90 mL): benzene (2 mL) to provide the title compound as a off-white solid (0.55 g, 39%): mp 104°–106° C.: NMR (DMSO, d $^6$): δ 13.1 (broad s, 1H, N$\underline{H}$), 8.10 (t, J=7.8 Hz, 1H, py$\underline{H}$), 7.95 (d, J=7.7 Hz, 1H, py$\underline{H}$), 7.71 (d, J=7.7 Hz, 1H, py$\underline{H}$), 7.45 (d, J=8.8 Hz, 2H, Ar$\underline{H}$), 7.35 (d, J=8.7 Hz, 2H, Ar$\underline{H}$), 3.86 (d, J=17.4 Hz, 1H, C$\underline{H}_2$), 3.72 (d, J=17.4 Hz, 1H, C$\underline{H}_2$), 2.57 (s, 3H, C$\underline{H}_3$); MS(EI): 420 (MI, 3%), 265 (12%), 263 (38%), 194 (25%), 192 (70%), 149 (40%), 93 (100%); Anal. Calc. for $C_{18}H_{13}ClN_2O_4S_2$: C, 51.37; H, 3.11; N, 6.66; Found: C, 50.99; H, 3.05; N, 6.58.

EXAMPLE 97

5-[3-(3,5-Bis(trifluoromethyl)phenyl)-prop-2-ynyl]-5-(0pyridine-2-sulfonyl)-thiazolidine-2,4-dione, (I)

By the procedure described in Example 43, this compound was prepared from 5-(Pyridine-2-sulfonyl)-thiazolidine-2,4-dione of formula (V). Example 19 and [3-(3,5-bis(trifluoromethyl)phenyl)-prop-2-ynyl]-bromide of formula (IX), Example 31: mp 150°–152° C.: NMR (DMSO, d $^6$): δ 8.79 (d, J=4.4 Hz, 1H, py$\underline{H}$), 8.16 (dr, J=1.6, 7.9 Hz, 1H, py$\underline{H}$), 8.11 (s, 1H, Ar$\underline{H}$), 8.05 (d, J=7.9 Hz, 1H, py$\underline{H}$), 7.94 (s, 2H, Ar$\underline{H}$), 7.9 (dd, J=4.9, 7.3 Hz, 1H, Ar $\underline{H}$), 3.87 (d, J=17.2 Hz, 1H, C$\underline{H}_2$), 3.71 (d J=17.2 Hz, 1H, C $\underline{H}_2$); MS(CI): 509 (MI+I, 100%), 367 (32%), 366 (352%), 287 (35%), 194 (25%), 194 (20%); Anal. Calc. for $C_{19}H_{10}F_6N_2O_4S_2$: C, 44.89; H, 1.98; N, 5.51; Found: C, 42.80; H, 2.09; N, 5.77.

EXAMPLE 98

5-(2,3-Dichlorothiophene-5-sulfonyl)-thiazolidine-2,4-dione, (V)

A solution of p-thiocresol (4.94 g, 39.8 mmol), triethylamine (5.55 mL, 39.8 mmol) in dichloromethane (30 mL) was added dropwise over 12 minutes to a solution of 2,3-dichlorothiophene-5-sulfonyl chloride (5.0 g, 19.9 mmol) in dichloromethane (50 mL) at –78° C. under a dry nitrogen atmosphere. An additional 10 mL of dichloromethane was added and the reaction mixture was stirred at –78° C. for 2 h and then warmed to room temperature over 20 minutes. The reaction mixture was poured into water (400 mL) and the layers were separated. The dichloromethane phase was washed with water (2×200 mL) and the combined aqueous phase was acidified with concentrated HCl. Solid NaCl was also added to the aqueous phase which was then extracted with ether (4×200 mL). The extracts were combined and dried ($Na_2SO_4$) and concentrated to afford 2,3-dichlorothiophene-5-sulfinic acid as a white solid (2.89 g, 67%): NMR (DMSO, d $^6$): δ 9.1 (broad s, 1H, O$\underline{H}$), 7.54 (s, 1H, thiophene $\underline{H}$); MS(EI): 216, 218, 220 (70, 50, 10%, MI), 199, 201, 203 (60, 50, 10%,—OH), 169 (50%), 167 (70%), 154 (70%), 152 (100%).This ulfinic acid (2.33 g, 10.73 mmol) was dissolved in a solution of sodium hydroxide (0.42 g, 10.73 mmol) in methanol (25 mL) at room temperature. The methanol was removed and residual water was removed by azeotroping with benzene to provide 2,3-dichlorothiophene-5-sulfinic acid, sodium salt of formula (IV) as a whir solid (2.57 g, 100%): NMR (DMSO, d$^6$): δ 6.89 (s, 1H, thiophene $\underline{H}$); Anal. Calc. for $C_4HCl_2O_2S_2$: C, 20.09; H, 0.41; Found: C, 19.80; H, 0.52. This sulfinic acid, sodium salt of formula (IV) (2.12 g, 8.87 mmol) was mixed with 5-bromo-thiazolidine-2,4-dione (1.58 g, 8.06 mmol) and Aliquat 336 (tricaprylylmethylammonium chloride, 0.45 mL) and allowed to stand overnight. Dilute aqueous HCl (100 mL) was added and the aqueous reaction mixture was extracted with ethyl acetate (2×100 mL). The combined extracts were washed with brine and concentrated. The crude product was purified by flash chromatography using acid washed (2% $H_3PO_4$ in methanol) silica gel and 82:18 ethyl acetate: petroleum ether as eluant to provide the title compound of formula (V) as a white solid: mp 176°–177° C: NMR (DMSO, d $^6$): δ 13.0 (broad s, 1H,N$\underline{H}$), 8.10 (s, 1H, thiophene $\underline{H}$); 6.85 (s, 1H, C$\underline{H}$); MS(E1): 331,333, 335 (30, 20, 5%, MI), 215, 217, 219 (100, 70, 15%); Anal. Calc. for $C_7H_3Cl_2NO_4S_3$: C, 25.31; H, 0.91; N, 4.22; Found: C, 25.83; H, 1.00; N, 4.23.

EXAMPLE 99

5-[3-(4-Chlorophenyl)-prop-2-ynyl]-5-(2,3-dichlorothiophene-5-sulfonyl)-thiazolidine-2,4-dione, (I)

By the procedure described in Example 96, this compound was prepared from 5-(2,3-dichlorothiophene-5-sulfonyl)-thiazolidine-2,4-dione of formula (V), Example 98 and 3-(4-chlorophenyl)-prop-2-ynyl]-bromide of formula (IX), from Example 21: mp 160°–160° C.: NMR (DMSO, d $^6$): δ

8.03 (s, 1H, thiophene $\underline{H}$), 7.44 (d, J=8.4 Hz, 2H, Ar$\underline{H}$), 7.33 (d, J=8.3 Hz, 2H, Ar$\underline{H}$), 3.69 (d, J=17.4 Hz, 1H, C$\underline{H}_2$), 3.52 (d, J=17.4 Hz, 1H, C$\underline{H}_2$); MS(−FAB): 478, 480 (10%, 10%, M−H), 297 (30%), 148 (100%); Anal. Calc. for $C_{16}H_8Cl_3NO_4S_3$: C, 39.97; H, 1.68; N, 2.91; Found: C, 40.30; H, 1.97; N, 2.95.

PHARMACOLOGY

The blood glucose lowering activity of the compounds of this invention were demonstrable in experiments using diabetic (db/db) mice.

The db/db (C57BL/KsJ) mouse exhibits many metabolic abnormalities that are associated with non-insulin dependent diabetes mellitus (Type II) in humans. The animals are obese, glucose intolerant and have fasting hyperglycemia which is sometimes accompanied by a paradoxical hyperinsulinemia. Furthermore, the db/db mouse will eventually develop some of the long-term complications that have been associated with diabetes mellitus. [See Coleman Diabetes, 31 (Suppl. 1 ), 1 (1982)]. In spite of these commonalities, the acute administration of sulfonylureas (even at extremely high dosages) will not reduce the hyperglycemia of the db/db mouse. [See Tutwiler et al, Diabetes 27, 856 (1978)]. The ability of a few other hypoglycemic agents to be effective in this species suggest that the other agents have mechanisms of action which are different from that of the sulfonylureas [ibid; Lee et al, Diabetes 31:12 (1982); Chang et al, Diabetes 32, 830 (1983); Hosokawa et al, Diabetes 34, 267 (1985)]. Such compounds, therefore, are more likely to be efficacious in the population of Type. II diabetic patients that do not respond to sulfonylurea therapy. The experiments are exemplified hereinbelow after the listing of the following general procedure pertaining to these experiments.

On the morning of Day 1, 35 mice [male db/db (C57BL/KsJ), Jackson Laboratories, 2 to 7 months of age and body weight 35 to 60 g] were fasted for 4 hours, weighed and a baseline blood sample was collected from the tail-tip of each mouse without anesthesia, placed directly into a fluoride-containing tube, mixed and maintained on ice. Food was then returned to the mice. The plasma was separated and levels of glucose in plasma determined by the Abbott VP Analyzer. Because of the variable plasma glucose levels of the db/db mice, 5 mice having the most extreme (i.e., highest or lowest) plasma glucose levels were excluded and the remaining 30 mice were 15 randomly assigned into 7 groups of equivalent mean plasma glucose levels:

| Group A: | Vehicle control | N = 6 |
| --- | --- | --- |
| Group B: | Positive control (ciglitazone) | N = 4 |
| Group C: | 1st Test drug | N = 4 |
| Group D: | 2nd Test drug | N = 4 |
| Group E: | 3rd Test drug | N = 4 |
| Group F: | 4th Test drug | N = 4 |
| Group H: | 5th Test drug | N = 4 |

On the afternoon of Days 1, 2 and 3 the vehicle, control or test drugs were administered (p.o.) to the ad libitum fed mice. The positive control, ciglitazone [(+)-5-[4-[(1-methylcyclohexyl)methoxy]benzyl]thiazolidine-2,4-dione] see Fujita et al, Diabetes, 32, 804 (1983), was given by gavage at a dose of 100 mg/kg/day. The test compounds were given by gavage at a dose of 100 mg/kg/day unless otherwise noted in the Table.

On the morning of Day 4, the mice were weighed and fasted, but water was available ad libitum. Three hours later, a blood sample was collected and then the mice were given the fourth administration of drug or vehicle. Blood samples were collected again from the unanesthetized mice at 2 and 4 hours after drug administration. The plasma was separated and levels of glucose in plasma determined by the Abbott VP Analyzer.

For each mouse, the percent change of it's plasma glucose level on Day 4 (mean of the 2 and 4 hour samples) from it's respective level before drug administration (Day 1 baseline sample) was determined as follows:

$$\frac{\text{Mean of 2 and 4 hour Samples (Day 4)}}{\text{Baseline Sample (Day 1)}} \times 100$$

Analysis of variance followed by Dunnett's multiple comparison (one-sided) was used to estimate the degree of statistical significance of the difference between the vehicle control group and the individual drug-treated groups. A drug was considered active, at the specific dosage administered, if the difference of the plasma glucose level has a $p<0.05$.

The tabulated results in the Table show that the 5-[3-aryl-prop-2-ynyl]-5-(arylsulfonyl)-thiazolidine-2,4-diones and 5-[3-aryl-prop-2-ynyl]-5-(arylsulfanyl)thiazolidine-2,4-diones of this invention show the property that they lower blood glucose levels in the postprandial diabetic (db/db) mice. The actual difference between the mean percent change of the vehicle and the drug-treated group is reported in the Table.

Examination of the results tabulated in the Table below shows that the compounds of this invention are well suited as antihyperglycemic agents for they lower blood glucose levels in diabetic mice. For example, the compounds of Examples 42, 43 and 81 at a dose of only 20 mg/kg give results comparable or superior to ciglitazone at 100 mg/kg.

| Biological Data/db/db Mouse | | |
| --- | --- | --- |
| | 4-Day-Postprandial db/db Mouse, % Decrease, Glucose | |
| Example | at 100 mg/kg dose | at 20 mg/kg dose |
| 36. | 35 | nt |
| 37 | 27 | nt |
| 38 | 19 | nt |
| 39 | a | nt |
| 40 | a | nt |
| 41 | a | nt |
| 42 | 79 | 31 |
| 43 | 55 | 38 |
| 44 | 20 | nt |
| 45 | 52 | 21 |
| 46 | a | nt |
| 47 | 43 | 23 |
| 48 | 36 | nt |
| 49 | 70 | 18 |
| 50 | 26 | nt |
| 51 | 69 | a |
| 52 | 58 | a |
| 53 | 65 | a |
| 54 | a | nt |
| 55 | 28 | nt |
| 56 | 43 | a |
| 57 | 45 | a |
| 58 | 24 | nt |
| 59 | 21 | nt |
| 60 | 36 | a |
| 61 | 53 | a |
| 62 | a | nt |
| 63 | 51 | 23 |
| 64 | 48 | a |
| 65 | 59 | a |
| 66 | 57 | 25 |

Biological Data/db/db Mouse

4-Day-Postprandial db/db Mouse, % Decrease, Glucose

| Example | at 100 mg/kg dose | at 20 mg/kg dose |
| --- | --- | --- |
| 67 | 54 | a |
| 68 | 33 | nt |
| 69 | 30 | nt |
| 70 | 25 | nt |
| 71 | a | nt |
| 72 | 30 | nt |
| 73 | 54 | 21 |
| 74 | 22 | NT |
| 75 | a | nt |
| 76 | 70 | a |
| 77 | 68 | a |
| 78 | 52 | a |
| 79 | 37 | nt |
| 80 | 64 | a |
| 81 | 67 | 36 |
| 82 | 56 | a |
| 83 | 33 | nt |
| 84 | a | nt |
| 85 | nt | a |
| 91 | 24 | nt |
| 92 | a | nt |
| 93 | a | nt |
| 94 | a | nt |
| 95 | a | nt |
| 96 | a | a |
| 97 | nt | a |
| 99 | nt | |
| ciglitazone* | 32[#] | a | nt — not tested
a — less than 15% decrease at dose tested
*reference standard
[#]mean of 38 experiments The blood glucose lowering activity of the compounds of this invention were also demonstrable in experiments using diabetic (ob/ob) mice.

The non-insulin dependent diabetic (NIDDM) syndrome can be typically characterizes by obesity, hyperglycemia, abnormal insulin secretion, hyperinsulinemia and insulin resistance. The genetically obese-hyperglycemic ob/ob mouse exhibits many of these metabolic abnormalities and is thought to be a useful model to search for hypoglycemic agents to treat NIDDM [Coleman, D.: Diabetologia 14: 141–148, 1978]. The experiments are exemplified hereinbelow after the listing of the following general procedure pertaining to these experiments.

In each study, mice [Male or female ob/ob (C57 B1/6J) mice and their lean litermates (ob/+ or +/+, Jackson Laboratories) ages 2 to 5 months (10 to 65 g)] of a similar age are randomized according to body weight into 4 groups of 10 mice. The mice are housed 5 per cage and are maintained on normal rodent chow with water ad libitum. Mice receive compound daily by gavage (suspended in 0.5 ml of 0.5% methyl cellulose); dissolved in the drinking water; or admixed in the diet. The dose of compounds given ranges from 2.5 to 200 mg/kg body weight/day. The dose is calculated based on the fed weekly body weight and is expressed as active moiety. The positive control, ciglitazone (5-(4-(1-methylcyclohexylmethoxy)benzyl)-2,4-dione, see Chang, A., Wyse, B., Gilchrist, B., Peterson, T. and Diani, A. Diabetes 32: 830–838, 1983.) was given at a dose of 100 mg/kg/day, which produces a significant lowering in plasma glucose. Control mice receive vehicle only.

On the morning of Day 4, 7 or 14 two drops of blood (approximetly 50 µl) are collected into sodium fluoride containing tubes either from the tail vein or after decapitation. For those studies in which the compound is administered daily by gavage the blood samples are collected two hours after compound administration.

The plasma is isolated by centrifugation and the concentration of glucose is measured enzymatically on an Abbott V.P. Analyzer.

For each mouse, the percentage change in plasma glucose on Day 4, 7 or 14 is calculated relative to the mean plasma glucose of the vehicle treated mice. Analysis of variance followed by Dunett's Comparison Test (one-tailed) are used to estimate the significant difference between the plasma glucose values from the control group and the individual compound treated groups ( CMS SAS Release 5.18). A compound will be considered active if the difference has a $p<0.05$.

Examination of the restfits tabulated in the Table below shows that the compounds of this invention are well suited as antihyperglycemic agents for they lower blood glucose levels in diabetic mice. For example, the compounds of Examples 49, 51 and 81 at a dose of only 50 mg/kg give results comparable or superior to ciglitazone at 100 mg/kg.

Biological Data/ob/ob Mouse

| Example | Dose mg/kg/day | 4 day-ob/ob Mouse, % Decrease, Glucose | % Decrease, Insulin |
| --- | --- | --- | --- |
| 45 | 100 | 40 | 65 |
| 49 | 50 | 47 | 56 |
| 51 | 50 | 36 | 69 |
| 53 | 50 | 30 | 30 |
| 81 | 50 | 44 | 57 |
| ciglitazone* | 100 | 43 | 39 |

*reference standard

What is claimed:

1. A 5-[3-Aryl-prop-2-ynyl]-5-(arylsufonyl)thiazolidine-2,4-dione or 5-[3-Aryl-prop-2-ynyl]-5-(arylsulfonyl)thiazolidine-2,4-dione of the formula:

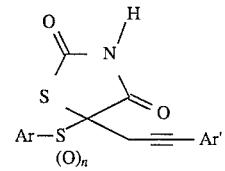

wherein

Ar is 3-pyridnyl, 4-pyridnyl or 2-pyridinyl optionally substiuted by —CH$_3$, n is 0 or 2; and Ar' is phenyl optionally substituted by halogen, —CF$_3$, —OCF$_3$, —SCH$_3$, —CH$_3$, or —OCH$_3$;

or a pharmaceutically acceptable salt thereof.

2. A 5-[3-Aryl-prop-2-ynyl]-5-(arylsufonyl)thiazolidine-2,4-dione or 5-[3-Aryl-prop-2-ynyl]-5-(arylsulfonyl)thiazolidine-2,4-dione of claim 1 wherein Ar is 2-pyridinyl;

n is 2; and

Ar' is phenyl optionally substituted by halogen, —CF$_3$, or —OCF$_3$;

or a pharmaceutically acceptable salt thereof.

3. A 5-[3-Aryl-prop-2-ynyl]-5-(arylsulfonyl)thiazolidine-2,4-dione of claim 1 which is 5-[3-(4-Chlorophenyl)-prop-2-ynyl]-5-(pyridine-2-sulfonyl)-thiazolidine-2,4-dione or a pharmaceutically acceptable salt thereof.

4. A 5-[3-Aryl-prop-2-ynyl]-5-(arylsufonyl)thiazolidine-2,4-dione of claim 1 which is 5-[3-(4-Fluorophenyl)-prop-2-ynyl]-5-(pyridine-2-sulfonyl)-thiazolidine-2,4-dione or a pharmaceutically acceptable salt thereof.

5. A method for treating hyperglycemia in a mammal, the method comprising administering to a mammal in need thereof a therapeutic dosage of a compound of the formula:

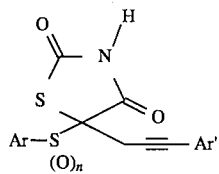

wherein
Ar is 3-pyridinyl, 4-pyridinyl or 2-pyridinyl optionally substituted by —CH$_3$;
n is 0 or 2; and
Ar' is phenyl optionally substituted by halogen, —CF$_3$, —OCF3, —SCH$_3$, —CH$_3$, or —OCH$_3$;
or a pharmaceutically acceptable salt thereof.

6. The method of claim 5 wherein:
Ar is 2-pyridinyl;
n is 2; and
Ar' is phenyl optionally substituted by halogen, —CF$_3$, or —OCF$_3$;
or a pharmaceutically acceptable salt thereof.

7. The method of claim 5 wherein the compound is 5-[3-(4-Chlorophenyl)-prop-2-ynyl]-5-(pyridine-2-sulfonyl)-thiazolidine-2,4-dione or a pharmaceutically acceptable salt thereof.

8. The method of claim 5 wherein the compound is 5-[3-(4-Fluorophenyl)-prop-2-ynyl]-5-(pyridine-2-sulfonyl)-thiazolidine-2,4-dione or a pharmaceutically acceptable salt thereof.

9. A pharmaceutical composition for relieving hyperglycemia in a mammal, the composition comprising a hyperglycemia relieving amount of a 5-[3-Aryl-prop-2-ynyl]-5-(arylsufonyl)thiazolidine-2,4-dione or 5-[3-Aryl-prop-2-ynyl]-5-(arylsulfanyl)-thiazolidine2,4-dione of the formula:

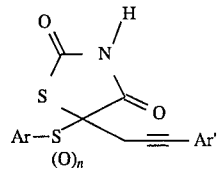

wherein
Ar is 3-pyridinyl, 4-pyridinyl or 2-pyridinyl optionally substituted by —CH$_3$;
n is 0 or 2; and
Ar' is phenyl optionally substituted by halogen, —CF$_3$, —OCF$_3$, —SCH$_3$, —CH$_3$, or —OCH$_3$;
or a pharmaceutically acceptable salt thereof.

* * * * *